United States Patent
Mendenhall

(10) Patent No.: US 6,602,365 B1
(45) Date of Patent: Aug. 5, 2003

(54) GAS GENERATION VIA METAL COMPLEXES OF GUANYLUREA NITRATE

(75) Inventor: Ivan V. Mendenhall, Providence, UT (US)

(73) Assignee: Autoliv ASP, Inc., Ogden, UT (US)

( * ) Notice: Subject to any disclaimer, the term of this patent is extended or adjusted under 35 U.S.C. 154(b) by 180 days.

(21) Appl. No.: 09/715,780

(22) Filed: Nov. 17, 2000

(51) Int. Cl.$^7$ .......................... C06B 31/00; C06B 31/28
(52) U.S. Cl. ............................. 149/45; 149/46
(58) Field of Search .............. 102/289; 149/45, 149/46; 280/736

(56) References Cited

U.S. PATENT DOCUMENTS

| | | | | |
|---|---|---|---|---|
| 2,604,391 A | * | 7/1952 | Taylor et al. ................... | 52/7 |
| 5,659,150 A | * | 8/1997 | Butt et al. .................. | 102/289 |
| 6,024,812 A | | 2/2000 | Bley et al. | |
| 6,039,820 A | | 3/2000 | Hinshaw et al. | |
| 6,117,255 A | | 9/2000 | Blomquist | |
| 6,132,538 A | | 10/2000 | Mendenhall et al. | |

FOREIGN PATENT DOCUMENTS

| DE | 195 31 288 A 1 | 2/1997 |
|---|---|---|
| EP | 519 485 | 6/1992 |
| FR | 360.787 | 5/1906 |
| FR | 919.287 | 3/1947 |

OTHER PUBLICATIONS

Begley, Michael J. et al., "Coordination Chemistry of Guanidine Derivatives Part 2. Crystal and molecular structures of bis (1–carbamoylguanidine) dinitratocopper (I I)", Database CA Online!, Database Accession No. 105:70458CA XP002200330 Abstract & J. Chem. Res., Synop. (1986).
Basil T. Fedoroff et al.: *Encyclopedia of Explosives and Related Items*, A210–A213, vol. 1, Picatinny Arsenal, Dover, New Jersey, 1960.

* cited by examiner

*Primary Examiner*—Michael J. Carone
*Assistant Examiner*—Aileen B. Felton
(74) *Attorney, Agent, or Firm*—Sally J. Brown; James D. Erickson

(57) ABSTRACT

Gas generant compositions are provided which compositions react to produce nitrogen gas and which compositions include at least one complex of guanylurea nitrate with at least one metal element having an atomic number of 21–30 and 39–50 and sufficient oxidizer such that, upon combustion reaction initiation of the gas generating composition, reaction products including a quantity of nitrogen gas are produced. Also, related methods of making a gas generating composition and associate methods of gas generation are provided.

29 Claims, 1 Drawing Sheet

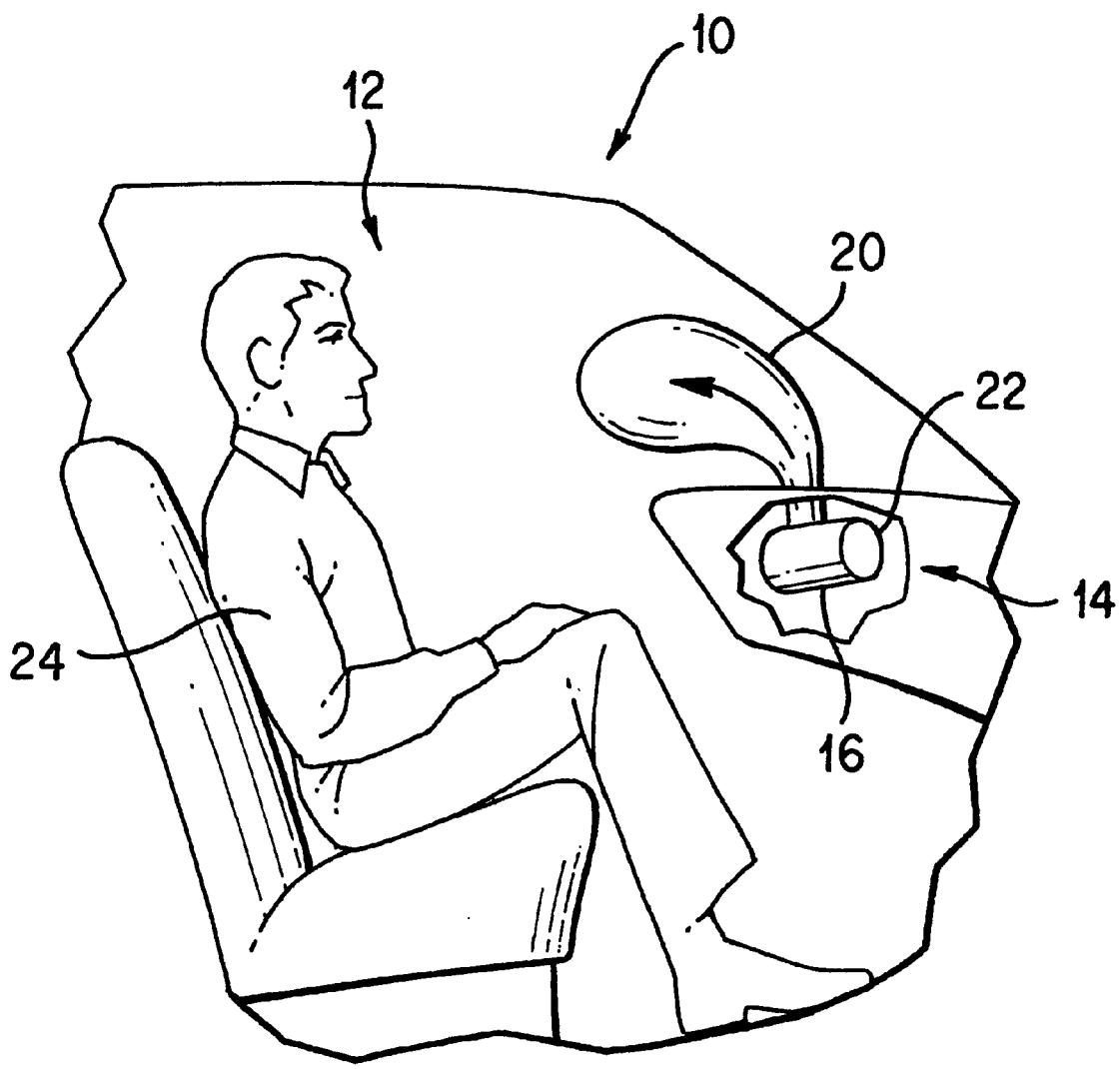
FIGURE

GAS GENERATION VIA METAL COMPLEXES OF GUANYLUREA NITRATE

BACKGROUND OF THE INVENTION

This invention relates generally to gas generation such as involved in the inflation of automotive inflatable restraint airbag cushions and, more particularly, to gas generant materials which contain metal complexes of guanylurea nitrate.

It is well known to protect a vehicle occupant using a cushion or bag, e.g., an "airbag cushion," that is inflated or expanded with gas when the vehicle encounters sudden deceleration, such as in the event of a collision. In such systems, the airbag cushion is normally housed in an uninflated and folded condition to minimize space requirements. Such systems typically also include one or more crash sensors mounted on or to the frame or body of the vehicle to detect sudden decelerations of the vehicle and to electronically trigger activation of the system. Upon system actuation, the cushion begins to be inflated in a matter of no more than a few milliseconds with gas produced or supplied by a device commonly referred to as an "inflator."

Gas generant compositions commonly utilized in the inflation of automotive inflatable restraint airbag cushions have previously most typically employed or been based on sodium azide. Such sodium azide-based compositions, upon initiation, normally produce or form nitrogen gas. While the use of sodium azide and certain other azide-based gas generant materials meets current industry specifications, guidelines and standards, such use may involve or raise potential concerns such as involving the safe and effective handling, supply and disposal of such gas generant materials.

In view thereof, significant efforts have been directed to minimizing or avoiding the use of sodium azide in automotive airbag inflators. Through such efforts, various combinations of non-azide fuels and oxidizers have been proposed for use in gas generant compositions. These non-azide fuels are generally desirably less toxic to make and use, as compared to sodium azide, and may therefore be easier to dispose of and thus, at least in part, found more acceptable by the general public. Further, non-azide fuels composed of carbon, hydrogen, nitrogen and oxygen atoms typically yield all gaseous products upon combustion. As will be appreciated by those skilled in the art, fuels with high nitrogen and hydrogen contents and a low carbon content are generally attractive for use in such inflatable restraint applications due to their relatively high gas outputs (such as measured in terms of moles of gas produced per 100 grams of gas generant material).

In addition to low toxicity and high gas outputs, fuel components for use in gas generant materials desirably are relatively inexpensive, thermally stable (i.e., desirably decompose only at temperatures greater than about 160° C.), and have a low affinity for moisture.

Oxidizers known in the art and commonly employed in such gas generant compositions are metal oxides or salts of oxygen-bearing anions (e.g., nitrates, perchlorates, etc.). During combustion, the metallic component of such oxidizers, however, typically ends up as a solid. Thus, the amount of oxidizer included in such gas generant materials can significantly effect the amount of gas produced upon combustion of the gas generant material. In view thereof, efforts have been directed to reducing or minimizing the amount of oxidizer required in such gas generant formulations. One approach used with at least some success in reducing or minimizing the required amount of oxidizer involves the incorporation of oxygen in greater relative amounts in the fuel component of the gas generant composition. Thus, desirable fuels for use in such gas generant compositions may preferably include a relatively high content of oxygen.

An additional complication results from the fact that at least certain transition metal-containing compounds or materials, such as commonly employed transition metal-containing oxidizers, may undesirably react with other composition materials to form metallic derivatives of a highly explosive nature and such as are unsuited for various general uses such as in an automotive inflatable restraint system or a gas generating device used in such a safety system. Thus, when including transition metal-containing compounds or materials in such formulations care is required to ensure that the formulation does not also include a material which may undesirably react therewith to form such explosive metallic derivatives.

U.S. Pat. No. 6,024,812 discloses propellant formulations which include nitroaminoguanidine as a main component, a secondary fuel or explosive ingredient such as dicyandiamidine nitrate (also known as "guanylurea nitrate") and an oxidizing agent. This patent discloses that oxidizing agents useful in the propellant formulation thereof include nitrates of alkali and alkaline earth elements, perchlorates of alkali and alkaline earth elements, ammonium nitrate, ammonium perchlorate or mixtures of these compounds.

Those skilled in the art will appreciate that nitroaminoguanidine exists in a form which has acid characteristics and can form metallic derivatives of a highly explosive nature. Thus, compounds or materials which contain a transition metal are incompatible with nitroaminoguanidine in known automotive inflatable restraint system gas generation applications.

In addition to the above-identified desirable properties and characteristics, gas generant materials for use in automotive inflatable restraint applications must be sufficiently reactive such that upon the proper initiation of the reaction thereof, the resulting gas producing or generating reaction occurs sufficiently rapidly such that a corresponding inflatable airbag cushion is properly inflated such as to provide impact protection to an associated vehicle occupant. In general, the burn rate for a gas generant composition can be represented by the equation (1), below:

$$Rb = Bp^n \tag{1}$$

where, $Rb$ = burn rate (linear)

$B$ = constant $P$ = pressure $n$ = pressure exponent, where the pressure exponent is the slope of the plot of the log of pressure along the x-axis versus the log of the burn rate along the y-axis Guanidine nitrate ($CH_6N_4O_3$) is a non-azide fuel with many of the above-identified desirable fuel properties or characteristics. For example, guanidine nitrate is commercially available, relatively low cost, non-toxic, provides excellent gas output due to a high content of nitrogen, hydrogen and oxygen and a low carbon content and has sufficient thermal stability to permit spray dry processing. As a result, guanidine nitrate has found wide use in the automotive airbag industry.

Unfortunately, guanidine nitrate suffers from a lower than may be desired burn rate. Further, guanidine nitrate may, when combined with certain other common gas generant formulation components, undesirably form eutectic mixtures. The lower melting points associated with such eutectic mixtures may in turn exacerbate concerns regarding the aging characteristics or properties of the gas generant formulation.

Thus, there remains a need and a demand for an azide-free gas generant material which may more effectively overcome one or more of the problems or shortcomings described above. In particular, there is a need and a demand for gas generant materials which, while effective in overcoming one or more of the problems or shortcomings identified above, also provides or results in a desirably rapid burn rate as required or desired for particular applications, while also avoiding formation of undesired eutectic mixtures.

SUMMARY OF THE INVENTION

A general object of the invention is to provide improved gas generation and, more particularly, to provide improved gas generant compositions and associated gas generant composition-containing devices and methods of gas generation.

A more specific objective of the invention is to overcome one or more of the problems described above.

In accordance with one preferred embodiment of the invention, the general object of the invention can be attained, at least in part, through a gas generating composition which includes a complex of guanylurea nitrate with at least one metal element having an atomic number of 21–30 and 39–50. The gas generating composition also includes sufficient oxidizer such that upon combustion reaction initiation of the gas generating composition reaction products including a quantity of nitrogen gas are produced.

The prior art generally fails to provide gas generant materials which, while avoiding inclusion or reliance on azide or azide-based materials, also suitably satisfies selected criteria such as relating to manufacture and performance. In particular, gas generant materials of the prior art and such as used in gas generating devices used in automotive inflatable restraint systems, for example, generally fail to provide or result in desirably high burn rates while avoiding undesired eutectic formation and while also satisfying, as effectively as desired, various manufacturing and performance criteria. For example and as described in greater detail herein, such manufacturing and performance criteria may include:
 a) avoidance of inclusion or reliance on azide or azide-based materials;
 b) cost;
 c) safety;
 d) gas output;
 e) thermal stability;
 f) effluent toxicity; and
 g) ease of manufacture or production via water-based processing.

The invention further comprehends a method of making a gas generating composition. In accordance with a preferred embodiment of this aspect of the invention such method involves contacting a quantity of guanylurea nitrate with a quantity of a complexing agent containing at least one metal element having an atomic number of 21–30 and 39–50 sufficient to form a complex of guanylurea nitrate containing the at least one metal element.

As described in greater detail below and in accordance with a preferred practice of such aspect of the invention, such contacting may desirably occur in a water slurry such as at an elevated temperature. Further, additional gas generant composition materials or components such as oxidizers, co-fuels, additives or combinations thereof can desirably be included in such gas generating composition via addition of the same to such slurry mixture.

The invention still further comprehends, in accordance with yet another embodiment of the invention, a method of generating gas wherein a gas generant composition which contains a complex of guanylurea nitrate with at least one metal element having an atomic number of 21–30 and 39–50 and sufficient oxidizer are reacted such that upon combustion reaction initiation of the gas generating composition reaction products including a quantity of nitrogen gas are produced.

As used herein, references to a specific composition, component or material as a "fuel" are to be understood to refer to a chemical which generally lacks sufficient oxygen to burn completely to $CO_2$, $H_2O$ and $N_2$.

Correspondingly, references herein to a specific composition, component or material as an "oxidizer" are to be understood to refer to a chemical generally having more than sufficient oxygen to burn completely to $CO_2$, $H_2O$ and $N_2$.

Guanylurea nitrate ($NH_2C(NH)NHC(O)NH_2 \cdot HNO_3$) is also commonly known as dicyandiamidine and amidinourea.

Other objects and advantages will be apparent to those skilled in the art from the following detailed description taken in conjunction with the appended claims and drawings.

BRIEF DESCRIPTION OF THE DRAWINGS

The FIGURE is a simplified schematic, partially broken away, view illustrating the deployment of an airbag cushion from an airbag module assembly within a vehicle interior, in accordance with one embodiment of the invention.

DETAILED DESCRIPTION OF THE INVENTION

The present invention provides gas generant materials such as may be used in the inflation of inflatable devices such as vehicle occupant restraint airbag cushions. Such gas generant materials typically include at least one complex of guanylurea nitrate with at least one metal element having an atomic number of 21–30 and 39–50 and sufficient oxidizer such that, upon combustion reaction initiation of the gas generating composition, reaction products including a quantity of nitrogen gas are produced.

For reasons such as relating to cost, availability, and low toxicity, preferred metal elements for use in the practice of the invention, include manganese, zinc and, in particular copper.

In gas generant compositions in accordance with the invention, the metal complex of guanylurea nitrate typically or primarily serves as a fuel material. In practice, preferred gas generant compositions in accordance with the invention contain or include fuel component in the range of about 20 to about 70 composition weight percent. Gas generant compositions in accordance with the invention may additionally contain or include one or more additional non-azide fuel material. For example, in accordance with certain preferred embodiments of the invention, gas generant compositions contain or include guanidine nitrate in addition to one or more metal complexes of guanylurea nitrate, as described above. Thus, in the general practice of the invention between about 10 up to 100 percent of the fuel material component constitutes one or more of such metal complexes of guanylurea nitrate. Those skilled in the art and guided by the teachings herein provided will be able to determine the appropriate relative amount of metal complex of guanylurea nitrate for inclusion in particular gas generant compositions dependent on factors such as desired relative burn rate and gas output. In particular, through the inclusion of a greater relative amount of such metal complex of guanylurea nitrate, compositions exhibiting higher relative burn rates may be realized. On the other hand, gas generant compositions having increased contents of such metal complex of guanylurea nitrate may, however, exhibit at least somewhat reduced gas outputs.

Various oxidizers, such as known in the art and either alone or in various combinations, can be used in the practice of the invention. For example and without unnecessary limitation on the broader practice of the invention, oxidizers such as selected from the group consisting of alkali metal nitrates, chlorates and perchlorates; alkaline earth metal nitrates, chlorates and perchlorates; transition metal oxides, basic nitrates, ammine nitrates, chlorates and perchlorates complexes; ammonium nitrates, either with or without phase stabilization; and mixture or combinations of two or more of such oxidizers, either from the same or different of such groups, may be used.

In accordance with certain preferred embodiments of the invention, about 30 to about 80 weight percent of the subject gas generant compositions generally constitutes such oxidizer component.

Gas generant compositions in accordance with the invention may also desirably contain one or more additives such as known in the art. Such additives typically function to satisfy one or more of the following conditions: increase the burn rate of the gas generant composition; improve the handling or other material characteristics of the slag which remains after combustion or reaction of the gas generant material; serve to cool the products formed upon reaction and improve either or both the ability to handle or process the gas generant material. For example, gas generant compositions in accordance with the invention may contain or include one or more additives such as silica and alumina, in a relative amount of between about 0 to about 10 weight percent, preferably in an amount of about 2 to about 5 weight percent, where such weight percentages are on the basis of the total gas generant material composition.

While the broader practice of the invention is not necessarily limited by the manner or technique by which such metal complex of guanylurea nitrate or associated gas generating composition is prepared or formed, in accordance with one preferred embodiment of the invention the subject metal complex of guanylurea nitrate can be formed by reacting guanylurea nitrate with an appropriate complexing agent containing at least one metal element having an atomic number of 21–30 and 39–50, such as a transition metal carbonate or basic metal carbonate, such as basic copper carbonate, in a aqueous slurry at an elevated temperature (e.g., T>50° C.). Such reaction is believed represented by the reaction (2), below:

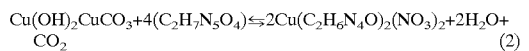
(2)

The copper complex of guanylurea nitrate, more specifically identified as copper II bis guanylurea dinitrate and commonly referred to as CuGUN, can be formed in good yield as withdrawal of liberated $CO_2$ pulls the reaction equilibrium towards the further formation of the complex product.

In accordance with a preferred practice of making or forming a gas generating composition containing such or similar metal complex of guanylurea nitrate, one or more oxidizer materials, such as described above, can be added to such slurry mix. Further, if desired, either or both one or more additional fuel materials (e.g., one or more "co-fuels"), such as described above, and one or more additives, such as also described above, can also be added to such slurry mix to form a gas generating composition having specifically desired performance characteristics or parameters.

Those skilled in the art and guided by the teachings herein provided will appreciate that the capability for a gas generant composition, including the oxidizer, to be processed via water-based processing has various practical and commercial benefits. For example, through the use of water-based processing, the components of the compositions can be mixed or otherwise processed with more uniformity such as to desirably result in less compositional variability. It is to be understood, however, that one or more metal complexes of guanylurea nitrate in accordance with the invention can be incorporated or included in various desirably formed or produced gas generant compositions and thus the broader practice of the invention is not necessarily limited to such a water-based slurry method of gas generant formation.

In accordance with a preferred practice of the invention, through the inclusion or use of such metal complexes of guanylurea nitrate in gas generant materials, reliance on the inclusion or use of sodium azide or other similar azide materials can be avoided while providing desirably sufficiently high or improved burn rates and overcoming one or more of the problems, shortcomings or limitations such as relating to cost, commercial availability, low toxicity, thermally stability and low affinity for moisture.

As will be appreciated, gas generating compositions in accordance with the invention can be incorporated, utilized or practiced in conjunction with a variety of different structures, assemblies and systems. As representative, the FIGURE illustrates a vehicle 10 having an interior 12 wherein is positioned an inflatable vehicle occupant safety restraint system, generally designated by the reference numeral 14. As will be appreciated, certain standard elements not necessary for an understanding of the invention may have been omitted or removed from the FIGURE for purposes of facilitating illustration and comprehension.

The vehicle occupant safety restraint system 14 includes an open-mouthed reaction canister 16 which forms a housing for an inflatable vehicle occupant restraint 20, e.g., an inflatable airbag cushion, and an apparatus, generally designated by the reference numeral 22, for generating or supplying inflation gas for the inflation of an associated occupant restraint. As identified above, such a gas generating device is commonly referred to as an inflator.

The inflator 22 contains a quantity of a gas generant composition in accordance with the invention and such as described above. The inflator 22 also includes an ignitor, such as known in the art, for initiating combustion of the gas generating composition in ignition communication with the gas generant composition. As will be appreciated, the specific construction of the inflator device does not form a limitation on the broader practice of the invention and such inflator devices can be variously constructed such as is also known in the art.

In practice, the airbag cushion 20 upon deployment desirably provides for the protection of a vehicle occupant 24 by restraining movement of the occupant in a direction toward the front of the vehicle, i.e., in the direction toward the right as viewed in the FIGURE.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

Comparative Example 1 and Examples 1–3

In each of these tests, gas generant material powders having the specific compositions shown in TABLE 1 were prepared, where numerical values refer to weight percentages. Samples of each of the specific compositions were press formed at 12,000 lbs. of force into slugs having a solid cylindrical shape 0.5 inch in diameter. These gas generant material slugs were then each evaluated for burn rate, as well as burn rate slope and constant. The results of such evaluation are shown in TABLE 2, below. TABLE 2 also includes density data and thermochemical data (e.g., gas yield in moles per 100 grams of generant, gas yield in moles per cubic centimeter generant, and flame temperature ($T_c$) in Kelvin) which was calculated in each case using the commercially available software program "PEP 1" (Propulsion Evaluation Program), compiled by Martin Marietta.

TABLE 1

| INGREDIENT | COMP. EXAMPLE 1 | EXAMPLE 1 | EXAMPLE 2 | EXAMPLE 3 |
|---|---|---|---|---|
| CuGUN | — | 10.00 | 20.00 | 30.00 |
| Guanidine nitrate | 51.72 | 42.07 | 32.30 | 22.66 |
| Basic copper nitrate | 45.28 | 44.93 | 44.70 | 44.34 |
| $Al_2O_3$ | 3.00 | 3.00 | 3.00 | 3.00 |

TABLE 2

| PARAMETER | COMP. EXAMPLE 1 | EXAMPLE 1 | EXAMPLE 2 | EXAMPLE 3 |
|---|---|---|---|---|
| BURN RATE | | | | |
| - Rb @ 1000 psi (inch/sec) | 0.50 | 0.55 | 0.61 | 0.66 |
| -slope | 0.354 | 0.374 | 0.362 | 0.421 |
| - constant | 0.044 | 0.041 | 0.050 | 0.036 |
| Gas yield (moles/100 g) | 2.92 | 2.82 | 2.73 | 2.63 |
| Density (g/cc) | 1.91 | 1.95 | 2.01 | 2.05 |
| Gas yield (moles/cc) | 0.0554 | 0.0552 | 0.0549 | 0.0539 |
| Flame Temp. $T_c$ (Kelvin) | 1868 | 1792 | 1709 | 1623 |

Discussion of Results

As the data in TABLE 2 shows, the gas generant inclusion and use of the copper complex of guanylurea nitrate (CuGUN), in accordance with the invention, resulted in compositions having increased burn rates. Additionally, the formulation inclusion and use of such metal complex of guanylurea nitrate resulted in formulations having the additional benefit of reduced flame temperature. As a result, such formulations would be expected to result in improved effluents, e.g., an effluent with a reduced $NO_x$ content. Further, as a result of the higher density of the compositions which contained the copper complex of guanylurea nitrate, CuGUN, in accordance with the invention, such guanylurea nitrate metal complex-containing compositions were found to supply a comparable volumetric gas output.

Thus, the invention provides a gas generating composition such as used in gas generating devices such as used in automotive inflatable restraint systems, which gas generant materials, while avoiding including or avoiding reliance on azide or azide-based materials, satisfies manufacturing and performance criteria such as relating to cost, safety, gas output, thermal stability, effluent toxicity and ease of manufacture or production via water-based processing, for example, in an effective manner while also providing or resulting in desirably high burn rates.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A gas generating composition comprising:
    at least one complex of guanylurea nitrate with at least one metal element having an atomic number of 21–30 and 39–50 and
    sufficient oxidizer such that upon combustion reaction initiation of the gas generating composition reaction products including a quantity of nitrogen gas are produced.

2. The gas generating composition of claim 1 wherein:
    the at least one complex of guanylurea nitrate includes copper.

3. The gas generating composition of claim 2 wherein:
    the at least one complex of guanylurea nitrate comprises copper II bis guanylurea dinitrate.

4. The gas generating composition of claim 1 wherein:
    the at least one complex of guanylurea nitrate includes zinc.

5. The gas generating composition of claim 1 wherein:
    the at least one complex of guanylurea nitrate includes manganese.

6. The gas generating composition of claim 1 having a fuel component including the at least one guanylurea nitrate metal complex in a relative amount of between about 20 to about 70 composition weight percent and the oxidizer in a relative amount of between about 30 to about 80 composition weight percent.

7. The gas generating composition of claim 6 wherein the fuel component additionally comprises at least one additional non-azide fuel material.

8. The gas generating composition of claim 7 wherein the at least one additional non-azide fuel material is guanidine nitrate.

9. The gas generating composition of claim 6 wherein the at least one metal complex of guanylurea nitrate comprises about 10 to 100 weight percent of the fuel component.

10. The gas generating composition of claim 9 wherein the at least one metal complex of guanylurea nitrate comprises copper II bis guanylurea dinitrate.

11. A gas generating device containing the gas generating composition of claim 1 in ignition communication with an ignitor for initiating combustion of the gas generating composition.

12. An automotive inflatable restraint system comprising:
the gas generating device of claim 11 connected with a collapsed inflatable airbag cushion to effect inflation thereof.

13. The gas generating composition of claim 2 having a fuel component including the at least one guanylurea nitrate metal complex in a relative amount of between about 20 to about 70 composition weight percent and the oxidizer in a relative amount of between about 30 to about 80 composition weight percent.

14. The gas generating composition of claim 13 wherein the fuel component additionally comprises at least one additional non-azide fuel material.

15. The gas generating composition of claim 14 wherein the at least one additional non-azide fuel material is guanidine nitrate.

16. The gas generating composition of claim 13 wherein the at least one metal complex of guanylurea nitrate comprises about 10 to 100 weight percent of the fuel component.

17. A gas generating device containing the gas generating composition of claim 2 in ignition communication with an ignitor for initiating combustion of the gas generating composition.

18. An automotive inflatable restraint system comprising:
the gas generating device of claim 17 connected with a collapsed inflatable airbag cushion to effect inflation thereof.

19. A gas generating composition comprising:
copper II bis guanylurea dinitrate and
sufficient oxidizer such that upon combustion reaction initiation of the gas generating composition reaction products including a quantity of nitrogen gas are produced.

20. The gas generating composition of claim 19 having a fuel component including the copper II bis guanylurea dinitrate in a relative amount of between about 20 to about 70 composition weight percent and the oxidizer in a relative amount of between about 30 to about 80 composition weight percent.

21. The gas generating composition of claim 20 wherein the fuel component additionally comprises at least one additional non-azide fuel material.

22. The gas generating composition of claim 21 wherein the at least one additional non-azide fuel material is guanidine nitrate.

23. The gas generating composition of claim 20 wherein the at least one metal complex of guanylurea nitrate comprises about 10 to 100 weight percent of the fuel component.

24. A gas generating device containing the gas generating composition of claim 19 in ignition communication with an ignitor for initiating combustion of the gas generating composition.

25. An automotive inflatable restraint system comprising:

the gas generating device of claim 24 connected with a collapsed inflatable airbag cushion to effect inflation thereof.

26. The gas generating composition of claim 1 wherein the oxidizer comprises ammonium nitrate.

27. The gas generating composition of claim 19 wherein the oxidizer comprises ammonium nitrate.

28. The gas generating composition of claim 1 wherein the oxidizer comprises basic copper nitrate.

29. The gas generating composition of claim 19 wherein the oxidizer comprises basic copper nitrate.

* * * * *